United States Patent [19]
Eyerer et al.

[11] Patent Number: 6,076,277
[45] Date of Patent: Jun. 20, 2000

[54] PROCESS FOR ENLARGING THE SURFACE OF PARTICLES

[75] Inventors: Peter Eyerer, Stupferich; Peter Elsner, Pfinztal; Rudolf Emmerich, Bruchsal, all of Germany

[73] Assignee: Fraunhofer-Gesellschaft zur Förderung der angewandtan Forschung e.V., München, Germany

[21] Appl. No.: 09/254,673

[22] PCT Filed: Sep. 25, 1997

[86] PCT No.: PCT/EP97/05263

§ 371 Date: Mar. 16, 1999

§ 102(e) Date: Mar. 16, 1999

[87] PCT Pub. No.: WO98/13132

PCT Pub. Date: Apr. 2, 1998

[30] Foreign Application Priority Data

Sep. 26, 1996 [DE] Germany .......................... 196 39 491

[51] Int. Cl.[7] ........................................ F26B 3/34
[52] U.S. Cl. ............................................. 34/263
[58] Field of Search .................. 34/245, 259, 263, 34/265, 279, 380, 381, 402; 219/687, 688, 689; 426/465, 289, 242, 640; 210/634, 137, 511

[56] References Cited

U.S. PATENT DOCUMENTS

| | | |
|---|---|---|
| 4,347,670 | 9/1982 | Wear et al. ............................... 34/263 |
| 4,513,513 | 4/1985 | Sayles . |
| 5,003,143 | 3/1991 | Marks et al. .......................... 34/263 X |
| 5,884,417 | 3/1999 | Pare ........................................... 34/263 |

FOREIGN PATENT DOCUMENTS

| | | |
|---|---|---|
| 0 085 014 | 8/1983 | European Pat. Off. . |
| 0 259 706 | 3/1988 | European Pat. Off. . |
| 0 514 775 | 11/1992 | European Pat. Off. . |
| 0 695 763 | 2/1996 | European Pat. Off. . |
| 23 27 956 | 12/1974 | Germany . |
| 32 33 819 | 3/1984 | Germany . |
| 56-035928 | 8/1981 | Japan . |
| 8-11 9697 | 5/1996 | Japan . |

*Primary Examiner*—Steve Gravini
*Attorney, Agent, or Firm*—Paul Vincent

[57] ABSTRACT

In order to enlarge the surface of particles which absorb liquids at least to a limited extent, the particles are exposed to a liquid or to a humid atmosphere containing this liquid at least until said liquid has penetrated into the area of the particles close to their surface, and the liquid-containing particles are then irradiated with micro-waves until the penetrated liquid evaporates. The surface of the particles is torn down to the depth of penetration of the liquid and thus enlarged, or the particles break up, creating small broken pieces with an irregular and enlarged surface.

6 Claims, No Drawings

PROCESS FOR ENLARGING THE SURFACE OF PARTICLES

BACKGROUND OF THE INVENTION

The invention concerns a method for reducing the size of polymer particles which absorb liquids to at least a certain extent, wherein the polymer particles are exposed to a liquid or to a damp atmosphere containing this liquid for a sufficient amount of time that the liquid penetrates at least into the region of the polymer particles proximate the surface.

The expression "polymer particle" means, within the current context, natural or synthetic thermoplastic, duroplastic or elastomer polymer particles obtained through polymerization, polycondensation or polyaddition, and which absorb arbitrary liquids to a certain extent.

Mechanical reduction in size of polymer particles of the above mentioned kind normally requires substantial technical effort and input of energy and is therefore expensive and time consuming. In addition, only those particles can be mechanically reduced in size which have a certain hardness and therefore a certain brittleness.

EP-A-0085014 describes a method for the reduction in size of elastic thermoplastic polymer particles such as polyethersulfone, polycarbonate or polysulfone. In this method, a solvent designated as a "tension split promoter", e.g. an acetone solution, diffuses into the surfaces of the polymer particles, wherein the structure of the particles is weakened along the diffusion path. The particles processed in this manner are subsequently subjected to an external mechanical force, e.g. a ball mill, wherein the coarse particles break up along the diffusion paths, defining lines of weakening, and smaller particles are obtained. The mechanical size reduction is therefore associated with a similar high energy input and high degree of technical difficulty and expense.

DE-A-2327956 describes a method for the production of water-soluble granulates containing hydratized salts, in particular granulated washing and cleaning agents. In order to obtain a granulate which does not bake together in bulk and which does not produce any hydratization heat, one uses a raw granulate containing a component suitable for hydratization while forming a product with a solid dry appearance (e.g. salts of polymer phosphoric acids, alcalicarbonates etc.) as well as water, wherein the water not only diffuses into the granulate but undergoes activated adsorption by effecting a change in the crystal water content of the water-soluble hydratized salts which are necessarily contained in the granulate. This raw granulate, of semi-solid damp manifestation, is expanded and solidified by microwave irradiation. There is no mention of reduction in size of the granulate.

Derwent abstract 81-69134 D of JP 56035928B discloses a method for the production of granulates made from powdered materials such as barium sulfate, aluminumsiliconoxide, instant coffee or powdered milk, wherein the powdered material is treated with a grid substance dissolved e.g. in water, ethanol or chlorated hydrocarbons which produces gas when heated, such as sodium hydrocarbonate or yeast and heated with microwave energy. The goal of this publication is to produce a granulate which is more porous than the initial powdered material for pharmaceuticals, food products etc. The initial powdered material should be wet with a sufficient amount of solution that it can evaporated in the microwave chamber. Granulation itself is done with conventional methods, wherein the microwave energy is solely utilized to drive out the gas producing substance. This publication also fails to mention any reduction in size of the granulate.

It is thereby the underlying purpose of the invention to propose a simple and economical method with the assistance of which polymer particles which absorb water to at least a limited extent can be reduced in size without using mechanical forces.

SUMMARY OF THE INVENTION

This purpose is achieved in accordance with the invention by a method for reducing the size of polymer particles which absorb liquids to at least a limited extent, wherein the polymer particles are subjected to a liquid or to a moist atmosphere containing this liquid for a sufficient length of time that the liquid penetrates at least into the regions of the particles proximate the surface in that the liquid-containing polymer particles are irradiated with microwaves until abrupt evaporation of the penetrated liquid, so that the associated spontaneous pressure increase in the molecular compound completely blows-up the structure of the polymer particles or does so only at the surface.

DESCRIPTION OF THE PREFERRED EMBODIMENT

The invention takes advantage of the absorption capability, possibly in the intermolecular region, of a plurality of polymers in order to enrich the presence of liquid in the polymer particles during a preparation process. This liquid is then rapidly boiled-off from the inside towards the outside using microwave energy. By means of the associated spontaneous pressure increase within the particle structure, possibly molecular compound, the particle structure is either completely blown-up or only at the surface. Water is primarily utilized, but any other liquid is also possible, in particular one having low viscosity and/or low boiling point. Microwaves having power ranges of 10 W to 50 kW are utilized in the method in dependence on the type of polymer particles and on other desired effects with regard to size reduction. The irradiation time can assume values between 1 s and several minutes.

The dwell time of the particles in the liquid or in the damp atmosphere can be used to approximately predict the penetration depth of the liquid for a given penetration coefficient so that the particle size of the polymer particles obtained subsequent to MW irradiation can also be approximately predicted.

In an embodiment of the invention, the polymer particles are subjected to liquid or to the damp atmosphere containing same for a sufficient amount of time that the liquid penetrates into the core of the particles. When such particles are irradiated with microwaves, they are completely blown-up by the formation of vapor and small pieces are obtained having large irregular surfaces. This method is particularly suited e.g. to obtain a fine-grained or powdered bulk material from coarse polymer particles. The procedure is particularly suitable when the polymer particles cannot be further reduced in size using conventional mechanical or chemical methods. This is the case for hard, for soft or for more or less ductile particles.

A plurality of polymers are known in the art which can absorb liquid or liquids, in particular water, to a greater or lesser degree. These include e.g. several thermoplastics, such as acrylate, polycarbonate and polyamide. With these polymers, the absorption of liquid generally leads to reduction in surface hardness.

In addition thereto, there are polymers which have been developed for the purpose of obtaining high absorption capability for liquids which transform into a gel-like state when the liquids are absorbed. These polymers are designated as super absorbent polymers (SAP). Such super absorbent polymers (SAP) are utilized in the form of beads, e.g. for the absorption of liquids in human applications with diapers, linings etc. These SAP particles are relatively expensive. The grain spectrum is primarily determined by the manufacturing process as are their relatively smooth surfaces. The method in accordance with the invention can be used to break-up surface regions of the beads. A surface area increase thereby results not only due to the production of bulk material but also through the production of ridged individual grains having corresponding increased surface areas. In this manner, the rate of absorption can be increased so that the SAP are either more effective or can be utilized in lower quantities. Practical experiments have shown that, in this application, microwave powers between 100 W to 5 kW under irradiation times between 1 s and 5 min and with a penetrated liquid level of 1 to 100% by mass have led to size reductions. One must simply cake care that the temperature increases within the particles occurring during irradiation do not lead to an undesired change in the molecular structure. This can be controlled via the power input and duration of irradiation as well as by the amount of penetrated liquid.

What is claimed is:

1. A method for reducing the size of liquid absorbing polymer particles comprising the steps of:

a) subjecting the particles to one of a liquid and a moist atmosphere containing said liquid;
   b) waiting a sufficient length of time such that said liquid penetrates into the polymer particles; and
   c) irradiating the particles, following step b), with microwaves to suddenly evaporate said liquid, wherein an associated spontaneous pressure increase in molecular compound of the polymer particles explodes a structure of the polymer particles.

2. The method of claim 1, wherein step c) comprise exploding said structure of the polymer particles proximate surfaces of the polymer particles.

3. The method of claim 1, wherein step c) comprises completely exploding the polymer particles.

4. The method of claim 1, wherein steps a) and b) comprise subjecting the polymer particles to one of said liquid and a damp atmosphere containing said liquid for a sufficient amount of time that said liquid penetrates only into regions proximate surfaces of the polymer particles.

5. The method of claim 1, wherein steps a) and b) comprise subjecting the polymer particles to one of said liquid and a damp atmosphere containing said liquid for a sufficient length of time that said liquid penetrates into a core of the polymer particles.

6. The method of claim 4, wherein step c) comprises producing polymer particles with roughened surfaces.

\* \* \* \* \*